United States Patent
Heimberger

[19]

[11] Patent Number: 5,807,241
[45] Date of Patent: Sep. 15, 1998

[54] BENDABLE TUBE AND METHOD FOR ITS MANUFACTURE

[75] Inventor: Rudolf Heimberger, Oberderdingen, Germany

[73] Assignee: Richard Wolf GmbH, Knittlingen, Germany

[21] Appl. No.: 711,834

[22] Filed: Sep. 10, 1996

[30] Foreign Application Priority Data

Sep. 22, 1995 [DE] Germany ............. 195 35 179.7

[51] Int. Cl.$^6$ ..................................................... A61B 1/00
[52] U.S. Cl. .......................................... 600/142; 600/139
[58] Field of Search .................... 600/138, 19, 141, 600/142, 144; 138/118, 120, 155, 166, 167, 168

[56] References Cited

U.S. PATENT DOCUMENTS

| | | | |
|---|---|---|---|
| 3,266,059 | 8/1966 | Stelle | 600/141 X |
| 4,108,211 | 8/1978 | Tanaka . | |
| 4,648,733 | 3/1987 | Merkt | 138/120 X |
| 4,651,718 | 3/1987 | Collins et al. | 600/142 |
| 5,143,475 | 9/1992 | Chikama | 600/141 X |
| 5,152,744 | 10/1992 | Krause et al. . | |
| 5,178,129 | 1/1993 | Chikama et al. | 600/142 |
| 5,448,989 | 9/1995 | Heckele | 600/142 |

FOREIGN PATENT DOCUMENTS

| | | |
|---|---|---|
| 0 612 496 A1 | 8/1994 | European Pat. Off. . |
| 0 626 604 A2 | 11/1994 | European Pat. Off. . |
| 69 38 905 | 1/1970 | Germany . |
| 18 16 973 | 2/1973 | Germany . |
| 17 66 209 | 7/1973 | Germany . |
| 24 47 510 A1 | 4/1975 | Germany . |
| 26 18 732 A1 | 11/1976 | Germany . |
| 43 17 914 A1 | 12/1994 | Germany . |

*Primary Examiner*—Beverly M. Flanagan
*Attorney, Agent, or Firm*—Panitch Schwarze Jacobs & Nadel, P.C.

[57] ABSTRACT

An bendable endoscope is disclosed which comprises tube sections. Neighbouring tube sections are completely materially separated from one another via a circumferential separating gap and are only connected to one another with a positive fit. By providing a corresponding number of tube sections, a flexible shank or a flexible shaft may be formed. The manufacture may be effected by laser cutting from a rigid tube.

18 Claims, 5 Drawing Sheets

BENDABLE TUBE AND METHOD FOR ITS MANUFACTURE

BACKGROUND OF THE INVENTION

The invention relates to a bendable tube, in particular as a shank for a flexible endoscope, as well as a method for manufacturing such a tube.

DESCRIPTION OF THE PRIOR ART

Fibrescopes according to the state of the art comprise at the distal end a highly flexible section which can be bent universally, in order for example, in a directed manner, to be able to visually inspect selected tissue regions or by way of additional auxiliary instruments, to be able to carry out therapy on these selected tissue regions, in a body cavity or likewise.

Moreover, shanks with a flexible section having cutting or milling instruments effective inside the body for minimal invasive surgery are known. With the latter, in spite of a laterally bent cutting head, a high force transmission must be possible, since the material to be treated, e.g. bone material may be hard and tough under certain circumstances.

With the endoscope known from the German utility model DE-U-3938905, a flexible section comprises a multitude of ring members which are axially in a row to one another and are connected to one another in an articulated manner. In the manufacture, the articulated connections must be separately mounted between the individual ring sections. A further flexible endoscope shank known from DE-C-1766209 comprises loose cylindrical sections lined up on four control wires i.e. the sections are not engaged with each other with a positive fit.

A further flexible endoscope tube arrangement, disclosed in DE-C-1816973, comprises tube sections arranged behind one another which non-positively engage inside one another by way of projections and recesses, but are releasable from one another.

Finally, from DE-A-2447510 there is disclosed a flexible endoscope shank comprising a cylindrical braiding on the outside of which there is arranged a multitude of bending elements engaging with one another. Each bending element comprises a projection at one end and a recess at the other end.

With all these known flexible shanks cited above there is the disadvantage that on the one hand the construction may be relatively complicated and on the other hand the manufacture can only be carried out in combination with additional parts for specific usage.

These known flexible endoscope shanks also therefore have the considerable disadvantage that their manufacture is complicated and, because of the constructional assembly, cost intensive. There is also the disadvantage with the manufacture of these known flexible endoscope shanks that a multitude of individual components must be manufactured and stored.

With the endoscope shank disclosed in US-A-5152744 which comprises a flexible section, the elastic deformability of the ordinarily rigid shank is achieved using selectively arranged recesses arranged in the wall of the shank and which are so formed that the individual sections are connected to one another with a material fit by webs having a certain width. As such there is however the danger that too strong a bending of the flexible section may lead to a rupture of one or more of the connecting webs.

SUMMARY OF THE INVENTION

It is the object of the present invention to provide a bendable tube, in particular as a shank for a flexible endoscope, which on the one hand avoids those disadvantages of the state of the art which have been previously mentioned, and on the other hand provides for a simple and therefore economic manufacture. Furthermore, those additional means for fastening individual tube sections are dispensed with, in order to be able to utilize the remaining free space within the tube as much as possible for other lumens, optical devices, mechanical devices and likewise. Moreover, a method is to be provided by which a bendable tube according to the invention can be inexpensively and simply manufactured.

That part of the above object with regards to the product is achieved in that the tube, where it is to be bendably formed, is formed from at least two tube sections which are materially separated from one another via a circumferential separating gap, but which are positively connected to one another at least in the direction of the longitudinal axis of the tube. The method part of the above invention is advantageously achieved by those features specified in claim 12, namely in that tube sections which are bendable to one another are formed from a rigid tube in which a circumferential gap is provided. At the same time the course of the separating gap is so chosen that neighbouring tube, sections although being materially separated from one another, are positively connected with one another.

The bendable tube according to the invention can practically be formed universally bendable, according to the arrangement and design of the separating gap. The positive connection between the neighbouring tube sections ensures that torsional, tensile and bending forces can be reliably accomodated, thus, with a corresponding design of the separating gap as is claimed in the dependent claims and described hereinafter, there results a bendable tube for almost any possible application case. Thus with a corresponding design of the positive connection elements, it is possible to permit the bending in only one plane or in several planes. Thus the bending may also permit the rotation of the tube in itself.

A bendable tube constructed according to the principle of the invention may however not only be applied to a shank of a flexible endoscope, but also to a variety of other applications. In the field of endoscope technology such a tube may for example be applied as a trocar sleeve, which is rigid during the actual piercing procedure and only becomes flexible after removing the trocar. Furthermore such a tube may be applied as reinforcement for a flexible tube on the outside or on the inside, it may serve as a universal drive replacement, or may be designed as a high frequency electrode. Such a tube may also be used as a chain, namely a hollow chain. Moreover an application as a stent, e.g. as a vessel support, oesophagus support or trachea support may also be possible. The flexible tube part formed by tube sections which are bendable to one another may be formed by a multitude of identical tube sections engaging with one another, this becoming particularly useful with regards to the manufacturing and the storage. However, varying tube sections may also be combined with one another, this not only being with regard to the axial length but also with regard to the design of the positive connection elements.

According to the invention, a bendable tube section comprises at least one lug facing the neighbouring tube section, said lug engaging into a corresponding recess of the neighbouring tube section with a positive fit. To form a flexible tube, several of such tube sections being bendable to one another are required. These tube sections having two neighbouring tube sections comprise, as seen with regards the axial direction of the tube, at least one lug on the one side, and to the other side a corresponding recess.

The previously mentioned design of a tube section having at least one lug represents the lower design limit with regard to the number of lugs. With regard to the robustness and flexibility it is generally better to provide each tube section with two or more lugs which engage into corresponding recesses of the neighbouring tube section. Preferably, with this, the lugs are so arranged that again a recess is formed between neighbouring lugs and into which a lug of the neighbouring tube section may engage. In this manner, a close interlocking of neighbouring tube sections is achieved in a simple design manner. The shape of the individual lugs and corresponding recesses depends on their function. At least one mushroom shaped lug is foreseen, in order to reliably ensure a positive fit with the neighbouring tube section by way of a corresponding recess in which this lug lies. The flexibility of the tube may on the one hand be determined by the shape of the lug and on the other by the width of the separating gap. In order to permit a selective bending, it is useful to provide the mushroom shaped lug with an outer contour which is part circular shaped at least in a sectioned manner.

In order to increase the torsional strength of such a tube and to permit bending for example in only one plane, it is useful to provide one or more rectangular lugs next to the previously mentioned mushroom shaped lug, these rectangular lugs corresponding to rectangular recesses into which they engage. Via such guiding lugs however, it is not compelling that the bendability be limited in direction, if these are to be displaced from one another as seen from the longitudinal axis of the tube. The displacement may be achieved in a simple manner in that at each tube section the recesses are displaced from the corresponding lugs by a certain angle. However, groups of differing sections may be provided which engage with each other alternately.

According to a further development of the invention, with a corresponding shaping of the lugs and recesses, not only can a bendable or flexible tube be produced, but also if then the lugs and recesses which engage with one other are provided with a. defined play in the undercut region in the axial direction, a tube which can also be altered in length can be provided. Such a length alignment may for example be useful then, when the tube is to be applied as a flexible shaft and an axial alignment similar to channel grooving or likewise is required.

In a further development of the invention, the mushroom shaped lugs and the correspondingly contoured recesses are aligned inclined to the longitudinal axis of the tube in a manner such that an imaginary axial projection of the lugs or recesses extends helically about the tube. If with such a design, again a defined play between the lugs and recesses in the region of the undercuts is envisaged, then by arranging tension and/or compression means within or outside the tube, a rotational movement is achieved by producing an axial motion. Therefore by then controlling the axial length of the tube, the twisting angle between the beginning and end of the tube may be selectively controlled.

The previously described tube sections for forming the bendable tube according to the invention may for example be economically manufactured in large numbers as injection mould parts, the arrangement of lugs and recesses being carried out such that an assembly is made possible be elastically bending up the tongues or recesses.

As a rule though, the method for manufacturing such a bendable tube which may for example be applied as a flexible endoscope shank, a hollow shaft, a chain, a flexible trocar, a stent or likewise, is much improved. Accordingly, a rigid tube is divided into the previously described tube sections using a separating method. In this case, an assembly of the tube sections to one another is dispensed with. The tube may be subject to a surface treatment for producing the separating gaps which simplifies the fabrication. With a suitable separating method it is not usually necessary to subject the individual tube sections to a subsequent treatment.

The manufacture of the separating gaps may principally be carried out using any conceivable cutting method. In particular, with thin walled tubes as are often used in endoscope technology, the separation using a laser beam is preferred, since with this a quick and economic manufacture is made possible without subsequent treatment of the separating gaps. With thick walled tubes having a larger diameter, the separating gaps may be achieved by milling or with even larger tubes by burning. Even here a subsequent treatment of the separating gaps may be dispensed with.

BRIEF DESCRIPTION OF THE DRAWINGS

The invention is hereinafter described in more detail by way of embodiments of the invention represented in the drawings. These show.

DETAILED DESCRIPTION OF THE PREFERRED EMBODIMENTS

With the separating method according to the invention, a separating gap is cut in a closed path in a rigid tube, this preferably being with a laser beam. With laser beam separation, a meander shaped separating gap for example, such as the gap 3 shown in FIG. 1 may be so cut into a rigid tube that connecting tube sections 1 and 2 arise (in FIG. 1 only two such tube sections are shown). With this, it is advantageous that the treatment and assembly of the individual tube section is finished with the completion of the laser cutting process i.e. without any further subsequent treatment, and that each individual section is comprised of a homogeneous wall thickness.

Figure 1:
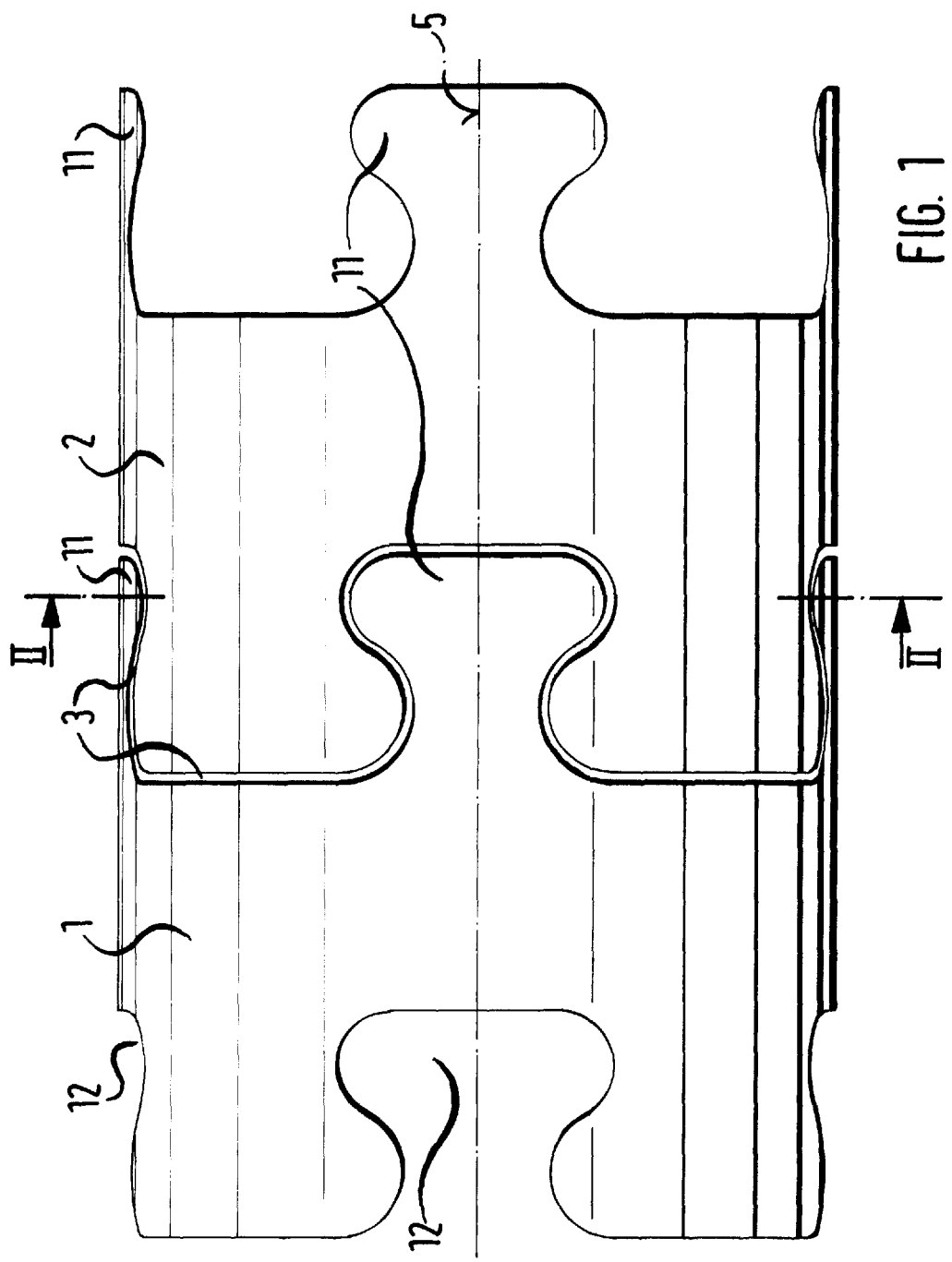
FIG. 1 a lateral view of two connected tube sections of a first embodiment form according to the invention which are produced by the separating method according to the invention.
Figure 2:
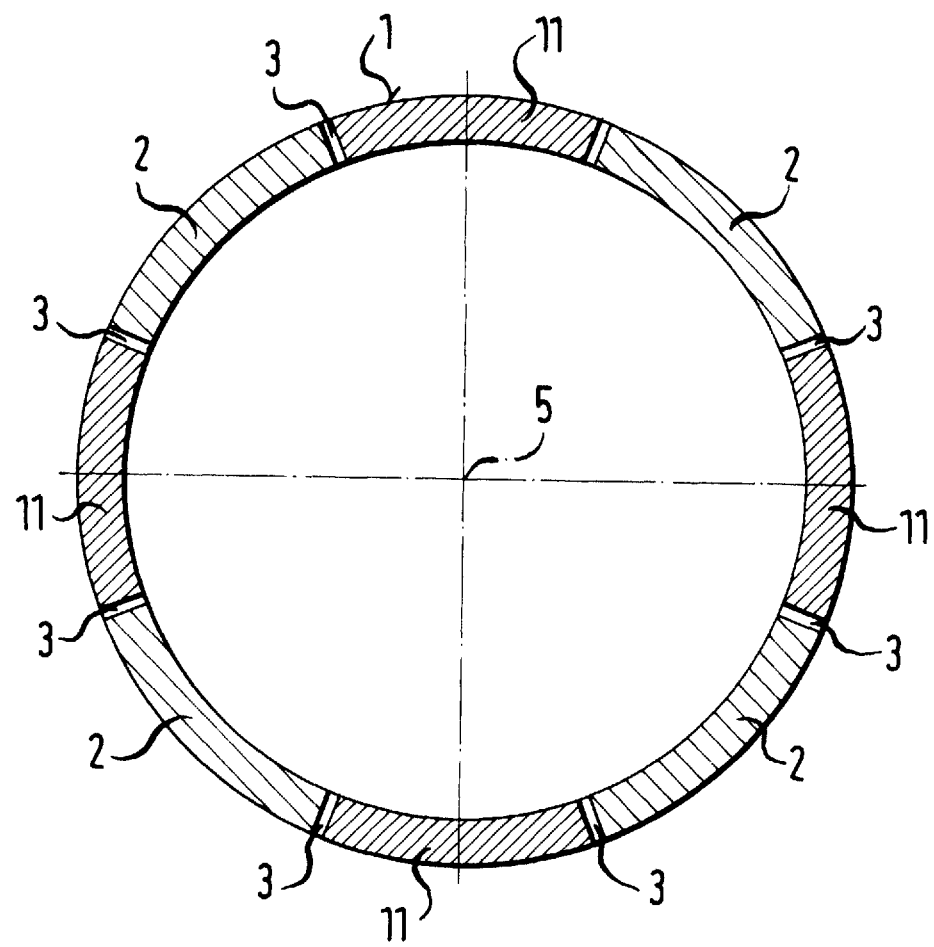
FIG. 2 a section through the sections shown in FIG. 1 along the section line II—II.

In combination with the cross-section shown in FIG. 2 through both tube sections 1 and 2 along the section line II—II shown in FIG. 1, it can be clearly seen that the cut gap 3, viewable on the elevation of the section II—II, seen in the circumferential direction, forms, on a tube section, four lugs 11 displaced about 90° and likewise four recesses 12 displaced about 90° and which essentially comprise the same mushroom shaped contour as the lugs 11. With each section 1, 2, each lug 11 lies opposite a respective recess 12 in the axial direction. As seen in the circumferential direction the recesses each form the undercuts of the lugs. In this way the individual sections may not be separated from one another without damaging. The degree of flexibility is dependent on the width of the separating gap 3, and on the length and the diameter of the individual element.

It is clear that number of lugs 11 and recesses 12 provided at one side is not limited to the number 4, there must however be at least one lug and one recess provided at one side of the tube section. With four lugs and recess alternating one another, a very good flexible bending in all planes in space can be achieved.

Furthermore, the separating gaps of a tube section comprising several sections may be so formed such that lugs and recesses neighbouring one another in the axial direction are displaced in the circumferential direction about a certain angle.

With the help of the division of a tube of a shank as is shown in FIGS. 1 and 2, flexible endoscope shanks, flexible trocar sleeves, flexible forceps, flexible technoscopes and flexible endoscopes as well as for instance flexible shanks for universally jointed shafts in bones and cartilage cuttings or universally jointed shafts per se may be manufactured.

Figure 3A:
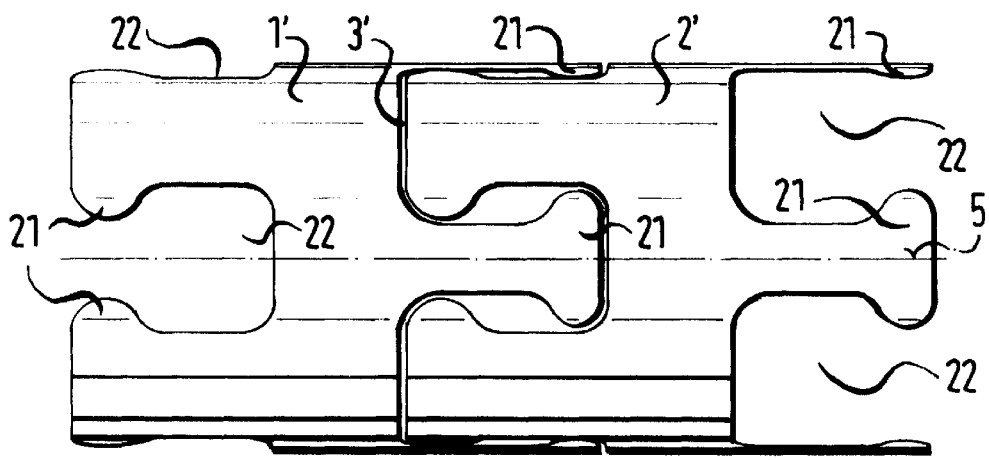
FIG. 3a a second embodiment form according to the invention of two sections in a first extended position of a flexible shank which are manufactured with the separating method according to the invention.
Figure 3B:
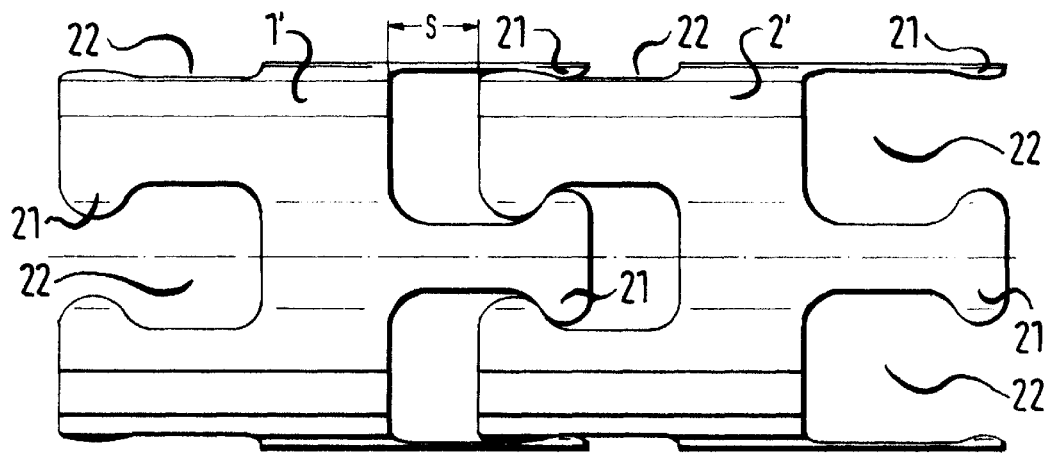
FIG. 3b the embodiment form according to FIG. 3a in a second extended position.

With the embodiment shown in FIG. 3a the separating gap 3' is so formed between two neighbouring identical tube sections 1', 2', that the lugs 21 lying in the recesses 22 have a defined distance from one another on account of the shape of their undercuts, so that a defined play S in the axial direction is guaranteed. In this way, such a designed flexible endoscope shank can be varied in length and is for instance advantageous in combination with instruments which by using inflatable and deflatable annular collars, undergo worm shaped movements to provide better indroduction into the gut or other body cavities with the aid of this instrument movement. FIGS. 3a and 3b show both sections 1' and 2' in both end positions, in which the flexible shank has its shortest or longest longitudinal extension. However on application of such tube sections 1', 2' as shown in FIG. 3a, where appropriate, an outer shank or other suitable guiding means is necessary in order to prevent sections neighbouring one another from being able to disengage, which is possible for example on bending. This for instance may also be prevented by a short thin walled ring cylinder part either outside or within the tube sections engaging one another.

Figure 3C:
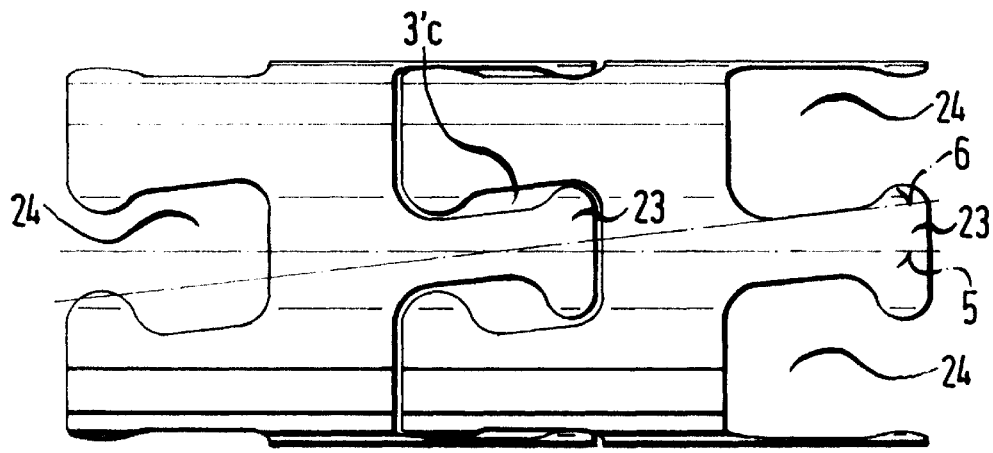
FIG. 3c an embodiment variation of this second embodiment form represented according to FIG. 3a, FIG. 4 a longitudinal section of a third embodiment of two sections connected with a positive fit and manufactured using the separating method according to the invention, FIG. 5 a lateral view of both sections according to FIG. 4, FIG. 6 a sectional representation according to FIG. 4 of the sections according to FIG. 4 in the bent condition, FIG. 7 a longitudinal section (section line VII—VII in FIG. 9) of a fourth embodiment of three sections connected with a positive fit and manufactured using the separating method according to the invention, in an extended position, FIG. 8 the embodiment according to FIG. 7 in the bent position and represented according to FIG. 7, FIG. 9 the embodiment according to FIG. 7 in a sectional representation (section line IX–IX in FIG. 7) rotated about 90° about the longitudinal axis and FIG. 10 the arrangement according to FIG. 7 in a bent position and represented according to FIG. 9.

With the embodiment shown by way of FIG. 3c there is not only an axial play S provided between the rear engagements which connect neighbouring tube sections with one another with a positive fit in the longitudinal direction of the tube, but furthermore the lugs 23 and the corresponding recesses 24 are inclined with regard to the longitudinal axis 5 of the tube in a manner such that an imaginary projection 6 of these lugs 23 or recesses 24 circulates the tube helically.

With such an arrangement the axial play S then serves not so much for the alignment of length, similar to channel toothing or likewise, but rather for producing a rotational movement. If namely the tube sections are moved from the shortest end position shown in FIG. 3c to the longest end position in which the lateral projections of the lugs 23 lie against those of the recesses 24, then the bending of the tube is effected about its longitudinal axis 5, this being between the end side tube sections. This bending about the longitudinal axis 5 may be used to produce a calculated rotational movement when corresponding tension and/or compression means are provided within or on the outside of the tube. With such an arrangement, an instrument for example may be rotated within a shank, without requiring a rotational movement for the control. The separating gap 3'c is thus, in contrast to the separating gap 3', arranged inclined to the axis 5 in the region of its longitudinal extension.

Figure 4:
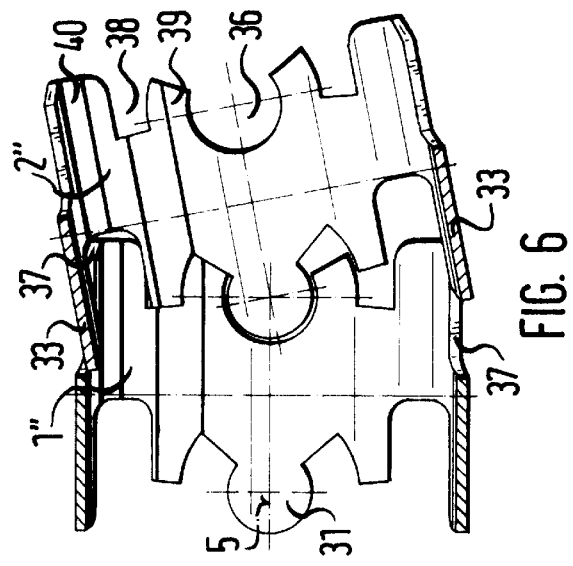
Figure 6:
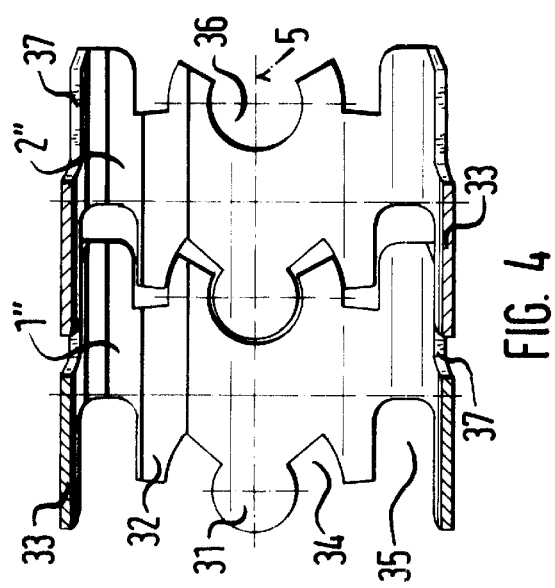
Figure 5:
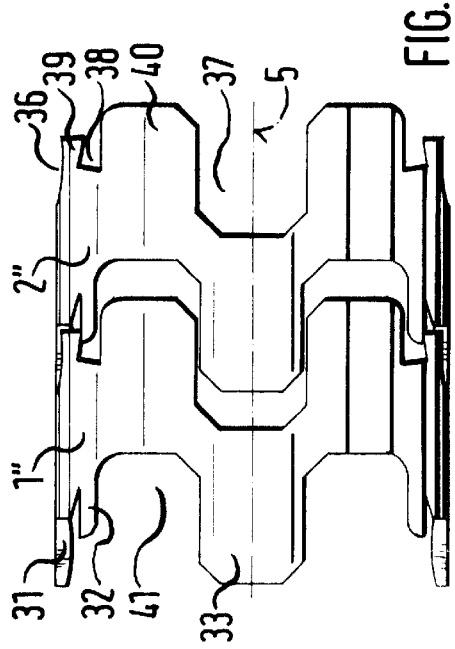
Figure 8:
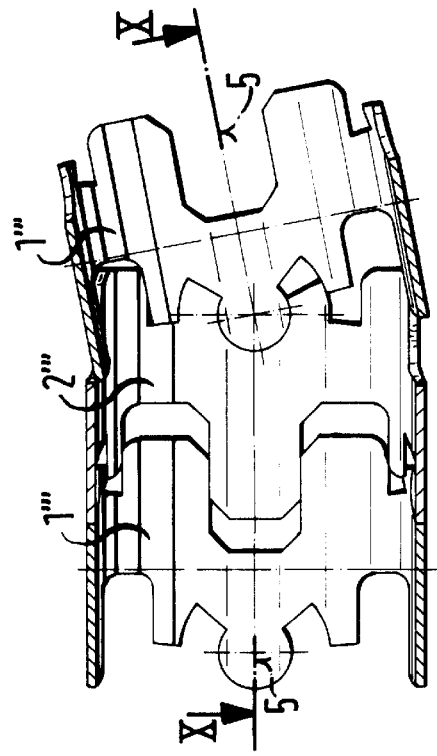
Figure 10:
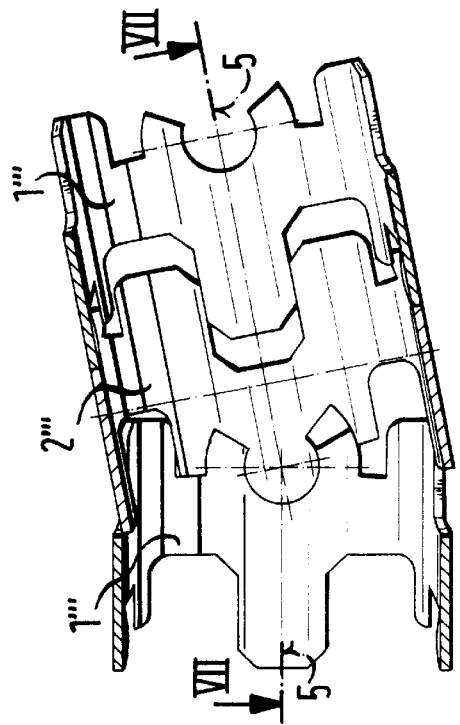
Figure 7:
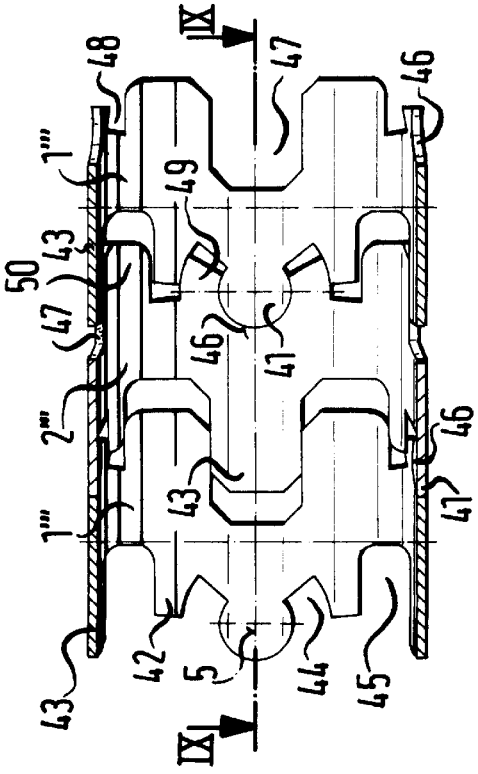
Figure 9:
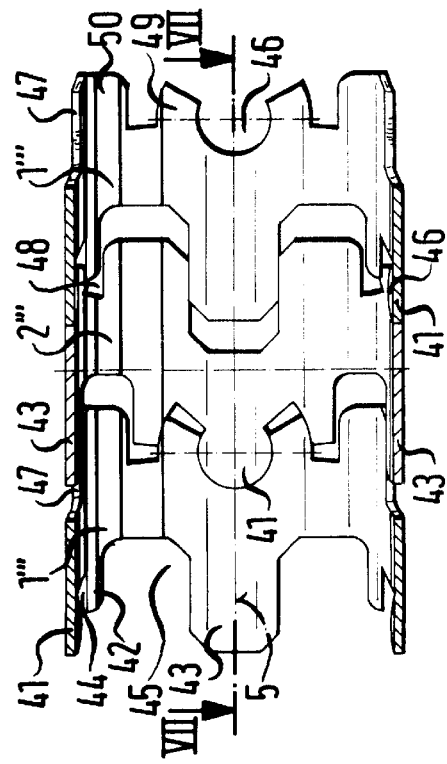

FIGS. 4 to 6 show two identical tube sections 1", 2" of a third embodiment form which engage into one another with a positive fit and which are cut from a rigid tube using the method according to the invention. Both tube sections 1", 2" comprise two first lugs 31 formed in an axial direction which have a part circular shaped contour and which are displaced to one another about 180° in the circumferential direction. In the same axial direction the tube sections comprise second lugs 33 having a rectangular contour and which are also displaced to one another by 180° and are each displaced about 90° with respect to the first part circular shaped lugs 31. Moreover both tube sections 1", 2" each comprise recesses 34, 35 between the first part circular shaped lugs 31 and the second rectangular shaped lugs 33, as well as a lug 32 arranged between both recesses which, with a suitable dimensioning of the lugs 31, 33, may also be omitted. The recess 34 undercuts the first lugs 31. In the other axial direction both tube sections 1", 2" comprise first recesses 36 with a part circular shaped contour which lie axially opposite to the first lugs 31. Further, both tube sections 1", 2" comprise second rectangular recesses 37 opposite the rectangular shaped second lugs 33 as well as additional recesses 38 which accomodate the lugs 32.

As is shown in FIG. 6, both sections 1", 2" may be bent to each other, the part circular shaped first lugs 31 of the second section 2" being pivotable with a positive fit in the part circular shaped first recesses 36 of the first section 1" as well as the second lugs 33 being pivotable with a positive fit in the rectangular shaped recesses 37, without these able to become disengaged. As such, a flexible shank section which is provided with tube sections 1", 2" according to FIGS. 4 to 6 may for instance be used as the distally controllable end part with flexible technoscopes and endoscopes, should a bending in only one plane be desired.

The embodiment variation represented by way of FIGS. 7 to 10 differs from that represented by way of FIGS. 4 to 6 in that the recesses of a tube section are arranged to the corresponding lugs of the same tube section not on the same axis, but arranged displaced about 90° to one another so that consecutive tube sections are always bendable in other planes.

In FIGS. 7 to 10 the neighbouring tub e sections are referred to at 1'" and 2'", in each case three tube sections are represented. Each tube section comprises on the left side two essentially rectangular lugs 43 which are displaced about 180° to one another. With this, the part circular shaped lugs 41 are each displaced about 90°. Lugs 42 are arranged between the lugs 41 and 43 and given a suitable dimensioning corresponding to the lugs 32 of the third embodiment form, may be omitted where appropriate. Between lugs 41 and 42 there are formed recesses 44 and between the lugs 42 and 43 recesses 45 are formed.

On the right side of FIGS. 7 to 10 the tube sections comprise essentially rectangular lugs 50 as well as pairs of lugs 49 arranged between these rectangular lugs. A part circular shaped recess 46 is formed between two lugs 49, and between two neighbouring lugs 50 is formed a rectangular recess 47. The part circular shaped recesses 46 which are displaced 180° to one another serve to receive the lugs 41 of the tube section neighbouring on the right side. This connection between the lugs 41 and the recesses 46 forms a articulating function about the common center axis of the lugs 41. Furthermore with these positive fit elements a positive fit in the direction of the longitudinal axis of the tube 5 or tube section is achieved. The rectangular lugs 43 together with the rectangular recesses 47 form guides which increase the torsional strength of the tube in the extended and bent conditions.

Because the recesses 46 corresponding to the lugs 41 or the recesses 47 corresponding to the lugs 43, these recesses being of the same tube section, are displaced about 90° to one another, there results an alternating bendability in one plane and subsequently in a plane displaced about 90° to this said one plane, by which means, with an adequate number of tube sections, a tube flexible in all directions is produced and which, with a compact construction, has a high inherent stability. The possible resulting larger bending radius compared to the third embodiment form (FIGS. 4 to 6) can at least be partly offset by shortening the tube sections, as is possible due to the displaced arrangement of recesses and lugs.

Common to all previously described embodiment forms is that the separating gap which is responsible for the movability of the individual tube sections is cut from a rigid shank tube using a laser beam cutting method. It is clear that the invention is not limited to the embodiment forms described by way of FIGS. 1 to 10. If for example the separating gap is so shaped such that it does not cut straight tube sections but inclined tube sections from the rigid shank, then an orientation of the flexible movability of the tube section or a defined curving of the same may be predetermined.

Furthermore, the tube sections according to FIG. 1 for example may be combined with those according to FIG. 3a or also FIGS. 4 to 10 in a movable shank part.

What is claimed is:

1. A bendable tube having a longitudinal axis (5) comprising tube sections (1,2) wherein neighboring tube sections (1,2) are materially separated from one another via a circumferential separating gap (3) but which are connected to one another with a positive fit at least in the direction of the longitudinal axis (5) of the tube, one of the neighboring tube sections (1) comprising at least one lug (11) facing the other of the neighboring tube sections (2), said lug being engaged into at least one corresponding recess (12) of the other of the neighboring tube sections (2) with a positive fit, said lug having a shape with undercuts, and said corresponding recess having a corresponding shape such that the recess forms the undercuts and interlocks with said lug.

2. A tube section for forming a bendable tube according to claim 1 at least one lug (11) is provided to one end side and to the other end side there is provided at least one recess (12) for receiving a lug with a positive fit.

3. A bendable tube section according to claim 1, further comprising at least one lug (11) having an approximate part circular shaped outer contour.

4. A bendable tube according to claim 1, further comprising at least one neighboring tube section (1) having at least two lugs (11) facing the other of the neighboring tube sections (2) and at least one corresponding recess (12) being formed by an intermediate space formed between two neighboring lugs (11) of the same tube section.

5. A bendable tube according to claim 1, wherein a lug (11) comprises a rounded, mushroom shaped outer contour.

6. A bendable tube according to claim 1, further comprising at least one lug (21) and at least one corresponding recess (22) having a distance (s) in a region of their rear engagements.

7. A bendable tube according to claim 1, wherein the neighboring tube sections (1,2) are formed from a single tube by the single tube being materially separated, with the lug and the corresponding recess of the neighboring tube sections being formed as the neighboring tube sections are materially separated.

8. A bendable tube having a longitudinal axis (5) comprising tube sections (1,2) wherein neighboring tube sections (1,2) are materially separated from one another via a circumferential separating gap (3), but which are connected to one another with a positive fit at least in the direction of the longitudinal axis (5) of the tube, one of the neighboring tube sections (1") comprising four or more lugs (31–33) facing the other of the neighboring tube sections (2").

9. A bendable tube according to claim 8, wherein at least one lug (33,40) comprises a rectangular outer contour.

10. A bendable tube according to claim 8, wherein one of the neighboring tube sections (1") comprises, to one side, two first lugs (31) arranged displaced about 180° having a part circular shaped contour and two second lugs (33) each arranged displaced about 90° to said two first lugs (31) and having a rectangular contour, and correspondingly formed recesses (35,36) to the other side.

11. A bendable tube having a longitudinal axis (5) comprising tube sections (1,2) wherein neighboring tube sections (1,2) are materially separated from one another via a circumferential separating gap (3), but which are connected to one another with a positive fit at least in the direction of the longitudinal axis (5) of the tube, at least one of the neighboring tube sections (1) comprising at least one lug (49,50) facing the other of the neighboring tube sections (2), said at least one lug engaging into at least one corresponding recess (44,45) of the other of the neighboring tube sections (2) with a positive fit, at least one of the neighboring tube sections having a first side and a second side, the at least one lug being located on the first side and a second recess being located on the second side, and the at least one lug being displaced about an angle with regard to the second recess.

12. A bendable tube having a longitudinal axis (5) comprising tube sections (1,2) wherein neighboring tube sections (1,2) are materially separated from one another via a circumferential separating gap (3), but which are connected to one another with a positive fit at least in the direction of the longitudinal axis (5) of the tube, at least one of the neighboring tube sections (1) comprising at least one lug (49,50) facing the other of the neighboring tube sections (2) and the other of the neighboring tube sections comprising at least one corresponding recess, said at least one lug (49,50) and the at least one corresponding recess (24) being so formed and arranged that an imagined longitudinal axis (6) extends helically about the longitudinal axis (5) of the tube.

13. A bendable tube according to claim 12, further comprising at least one neighboring tube section (1) having two or more lugs facing the other of the neighboring tube sections (2).

14. A method for manufacturing a bendable tube which is flexible at least section-wise, comprising separating an essentially rigid tube having a longitudinal axis (5) into tube sections (1,2) so that tube sections (1,2) are completely materially separated from one another by a separating gap, and selecting a course of the separating gap between neighboring tube sections such that the neighboring tube sections are connected to one another with a positive fit at least in the direction of the longitudinal axis (5) of the tube.

15. A method according to claim 14, wherein selecting said course of the separating gap further comprises forming at least one lug having a shape with undercuts, and simultaneously forming a corresponding recess having a corresponding shape such that the recess forms the undercuts of the lug and interlocks with said lug.

16. A method according to claim 14, wherein the bendable tube is an endoscope.

17. A method according to claim 14, wherein the separating is effected by a laser beam.

18. A method according to claim 14, wherein the separating is effected chemically or electrochemically.

* * * * *